US011707435B2

(12) United States Patent
Meissner et al.

(10) Patent No.: US 11,707,435 B2
(45) Date of Patent: **\*Jul. 25, 2023**

(54) GATE FOR A TABLET DISCHARGE OF A TABLET PRESS, AND METHOD FOR ACTUATING A GATE

(71) Applicant: Fette Compacting GmbH, Schwarzenbek (DE)

(72) Inventors: Friedrich Meissner, Schwarzenbek (DE); Stefan Luedemann, Hamburg (DE)

(73) Assignee: Fette Compacting GmbH, Schwarzenbek (DE)

( * ) Notice: Subject to any disclaimer, the term of this patent is extended or adjusted under 35 U.S.C. 154(b) by 190 days.

This patent is subject to a terminal disclaimer.

(21) Appl. No.: 16/458,686

(22) Filed: Jul. 1, 2019

(65) Prior Publication Data

US 2020/0009058 A1   Jan. 9, 2020

(51) Int. Cl.
*A61K 9/20* (2006.01)
*B30B 11/00* (2006.01)
*B30B 11/02* (2006.01)
*B30B 15/30* (2006.01)
*B30B 15/32* (2006.01)

(52) U.S. Cl.
CPC .............. *A61K 9/20* (2013.01); *B30B 11/005* (2013.01); *B30B 11/02* (2013.01); *B30B 15/304* (2013.01); *B30B 15/32* (2013.01)

(58) Field of Classification Search
CPC ..... B30B 11/005; B30B 11/02; B30B 15/304; B30B 15/32
See application file for complete search history.

(56) References Cited

U.S. PATENT DOCUMENTS 4,066,173 A * 1/1978 Adams ................. B30B 11/005
377/6
2008/0237097 A1   10/2008   Kolbe et al.

FOREIGN PATENT DOCUMENTS

| CN | 205112500 U | 3/2016 |
| EP | 1974895 A2 | 1/2008 |
| EP | 2368704 A2 | 9/2011 |
| JP | 2001511708 A | 8/2001 |

(Continued)

OTHER PUBLICATIONS

Fette Compacting GmbH; JP Application No. 2019-116856; Office Action dated Sep. 7, 2020 (5 pages).

*Primary Examiner* — Yung-Sheng M Tsui
(74) *Attorney, Agent, or Firm* — Barclay Damon LLP

(57) ABSTRACT

A tablet press comprises a gate and a control apparatus configured to generate a switching signal. A drive apparatus is configured to move the gate in response to the switching signal received from the control apparatus between a first switching position and at least a second switching position. At least one sensor is configured to generate a detection signal when the gate reaches one of the switching positions. The control apparatus receives the detection signal and is configured to output a switching signal to the drive apparatus to at least partially move the gate back into a home position when there is a switching signal to move the gate out of the home position and there is no detection signal received from the at least one sensor. The control apparatus subsequently outputs a switching signal to again move the gate out of the home position to a target position.

9 Claims, 2 Drawing Sheets

(56) References Cited

FOREIGN PATENT DOCUMENTS

| JP | 2011235332 A | 11/2011 |
|---|---|---|
| KR | 2020140002859 | 6/2014 |
| WO | 9835822 | 8/1998 |
| WO | 2008/038070 A1 | 4/2008 |
| WO | 2018/2032758 A1 | 11/2018 |

* cited by examiner

GATE FOR A TABLET DISCHARGE OF A TABLET PRESS, AND METHOD FOR ACTUATING A GATE

CROSS REFERENCE TO RELATED INVENTION

This application is based upon and claims priority to, under relevant sections of 35 U.S.C. § 119, German Patent Application No. 10 2018 116 202.2, filed Jul. 4, 2018, the entire contents of which are hereby incorporated by reference.

BACKGROUND

The invention relates to a gate for a tablet discharge of a tablet press, in particular a rotary tablet press, wherein a control apparatus is provided, and wherein a drive apparatus is provided that moves the gate, depending on a switching signal from the control apparatus, between a first switching position in which tablets are fed to a first tablet outlet, and at least one other switching position, such as a second switching position in which tablets are fed to at least one second tablet outlet, wherein at least one sensor is provided for detecting the reaching of the first switching position and the at least one second switching position by the gate.

The invention moreover relates to a method for actuating a gate for a tablet discharge of a tablet press, in particular a rotary tablet press, in which the gate is moved between a first switching position in which tablets are fed to a first tablet outlet, and at least a second switching position in which tablets are fed to at least one second tablet outlet, wherein the reaching of the first switching position and at least the second switching position by the gate is detected by means of at least one sensor.

Rotary tablet presses have a plurality of upper and lower punches which are always assigned in pairs to a cavity of a die plate of a rotor of the rotary tablet press. While the rotor is rotating, the cavities are filled with the filling material to be pressed. In at least one pressing apparatus, the upper and lower punches are pressed against each other in the cavities to press the filling material into tablets. After pressing, the tablets are generally ejected out of the cavities by the lower punch and, for example, supplied by a scraper to a tablet discharge. The removed tablets are for example fed to different tablet outlets by using measured values from sensors of the rotary tablet press, for example tablet outlets for good tablets, for bad tablets, or for tablets for a sampling. To guide the tablets into different tablet outlets, gates are regularly found in tablet discharges of rotary tablet presses. Such gates can for example have a gate flap that is pivotably movable between for example two switching positions which direct the tablets, depending on the switching position, to a first tablet outlet or a second tablet outlet.

It is known to detect when the respective end positions of the gate are reached by means of sensors. Generally two sensors are provided for detecting the respective end position for a gate with two switching positions. If the sensors recognize that an end position has not been reached, a corresponding error message is output.

Corresponding to the high production capacities of modern rotary tablet presses, a significant flow of tablets flows through the tablet discharge. In so doing, the tablets regularly flow with only a slight distance between each other. When switching the gate, this can lead to a clamping of tablets between the gate, for example the free end of a gate flap, and an opposite wall of the tablet discharge. Correspondingly, the gate cannot reach its target switching position. This can in turn lead to a tablet jam in the tablet discharge, and to a shutoff of the rotary tablet press due to a gate malfunction. This significantly restricts the availability of the rotary tablet press, and the manual effort for an operator to eliminate the malfunction is high. To eliminate a tablet jam, it is accordingly necessary to open the housing of the rotary tablet press which leads to an elevated health risk, in particular when the pressing materials are toxic. Moreover, it is regularly necessary to remove components such as the gate drives, the column of air, covers, etc. to make the region of the tablet jam accessible. The jammed tablets must be removed as well as any fragments, and the tablet discharge must be cleaned. Moreover, it must be checked whether any bad tablets or fragments have unintentionally entered into good production. Then the removed components must be remounted, and the rotary tablet press must be restarted.

Starting from the explained state of the art, the object of the invention is to provide a gate and a method of the aforementioned type by means of which the availability of the rotary tablet press is maximized even with high production capacities, and the effort and health hazard for operators is minimized.

BRIEF SUMMARY OF THE INVENTION

For a gate of the aforementioned type, the invention achieves the object in that detection signals from the at least one sensor are applied to the control apparatus, and the control apparatus is designed to output a switching signal to partially or completely move the gate back into the home switching position when there is a switching signal to move the gate out of a home switching position into a target switching position and when there is no detection signal for reaching the target switching position, and then to output a switching signal to again move the gate into the target switching position.

For a method of the aforementioned type, the invention achieves the object in that, when the reaching of the target switching position is not detected during a movement of the gate from a home switching position into a target switching position, the gate is partially or completely moved back into the home switching position, and then moved again into the target switching position.

The gate can be moved between a first switching position that for example can form a home switching position, and at least one second switching position that for example can form a target switching position. The first switching position and the at least one second switching position, or respectively the home switching position and the target switching position, are each end positions of the gate, or respectively a gate flap of the gate. In these end positions, a separation between the discharge channels of the gate and hence a guidance of the stream of tablets into the desired tablet outlet are ensured. In at least one end position, the gate, or respectively a gate flap, can for example lie against an inner wall of a discharge channel of the tablet discharge. In at least one end position, it can however also form part of a partition wall between different discharge channels of the tablet discharge.

A control apparatus is provided for the gate according to the invention that emits a switching signal to move the gate between a first switching position and at least one other switching position, such as a second switching position. The control apparatus can emit the switching signal for example due to measured values from sensors of the tablet press, or due to inputs to take a sampling. For example, sensors of the rotary tablet press can recognize impermissible deviations of parameters by produced tablets. These measured values can be applied to the control apparatus, and the control apparatus can correspondingly output a switching signal to move the gate into a switching position in which the corresponding tablets are fed to a tablet outlet for bad tablets. When there is a signal for taking a sampling, the control apparatus can also output a switching signal to move the gate into a switching position in which a given tablet quantity is fed to a tablet outlet for sampling, i.e., a spot check. The control apparatus can simultaneously be the control apparatus for controlling the operation of the rotary tablet press (machine control). It can however also be a control apparatus separate from such a machine control.

Moreover, a drive apparatus is provided that moves the gate depending on the switching signal received from the control apparatus into the desired switching position. The drive apparatus can for example comprise an electric motor which moves the gate between the first and the at least one second switching position, for example pivots a gate flap. Electromagnetic drives would, for example, however also be conceivable. In a manner known per se, at least one sensor is also provided that detects one or more, in particular all end positions of the gate, i.e., the first and/or the at least one second switching position, or respectively the home switching position and the target switching position. Several sensors can be provided for this. In so doing, the end positions can be detected directly or indirectly. For example, the sensor or the sensors can also deduce from other measured values when the respective end position is reached or not reached. For example, induction sensors or microswitches are possible as sensors which recognize when each given end position is reached or not reached. Of course, they can also be different sensors. An angle sensor is also cited as an example that detects the angular position of the gate such as a gate flap, and accordingly can detect all the end positions and preferably also any intermediate positions of the gate.

During a movement of the gate out of a home switching position such as the first switching position into a target switching position such as the at least one second switching position, the at least one sensor detects whether or not the target switching position was reached. The measuring signals from the at least one sensor are applied to the control apparatus. If the reaching of the target switching position is not detected by the at least one sensor despite a switching signal from the control apparatus to move the gate out of a home switching position into the target switching position, the control apparatus emits a switching signal to the drive apparatus to partially or also completely move the gate back toward the home switching position. Correspondingly, the drive apparatus partially or completely returns the gate toward the home switching position while reversing its direction of movement. Then the control apparatus emits a switching signal to the drive apparatus to (again) move the gate back into the target switching position while again reversing the direction of movement. The drive apparatus correspondingly returns the gate back into the target switching position. For example, a critical time period after the switching signal has been output can be specified within which the detection signal from the at least one sensor for reaching the target switching position must be present. If this critical time period is exceeded without the detection signal for reaching the target switching position being present, the gate is partially moved back. This critical time period can for example be chosen to be slightly greater than the time period needed to switch the gate out of the home switching position into the target switching position.

The invention is based on the idea that a tablet is clamped between the gate and a wall of the tablet discharge when there is no detection signal for reaching the target switching position. In order to release this clamped tablet for a discharge, the gate is moved back toward its home switching position. The tablet clamped between the gate, for example a gate flap, and an opposite wall of the tablet discharge, is accordingly released to flow out, and the gate can then safely assume the target switching position.

The invention accordingly assumes that a clamping of tablets can still occur. However, measures are pursued to immediately and automatically have the control apparatus eliminate the existence of such clamping. In particular when the specified end position of the gate is not reached, this information is used to reverse the direction of movement of the gate. By reversing the direction of movement, clamped tablets are released and can leave the gate region. Then the end position can be reliably approached.

Since any clamping of tablets is directly and automatically eliminated according to the invention, a tablet jam in the tablet discharge with the explained negative consequences can be reliably prevented. A gate malfunction which in practice is one of the most frequent reasons for the stoppage of a rotary tablet press is prevented or at least attenuated such that subsequent problems like a tablet jam and the associated consequences do not occur.

Since a tablet jam is prevented, the reliability and availability of the rotary tablet press is increased. Operators are protected from toxic products and associated health risks by automatically eliminating the gate malfunction. Manual effort to eliminate a gate malfunction is avoided. Furthermore, since a stoppage of the rotary tablet press and a subsequent starting process can be avoided, the arising waste is significantly reduced in comparison to the prior art. Moreover, increased tablet quality can be achieved by reduced mechanical stress on the tablets.

The explained method for eliminating a clamping of tablets can be repeated until the reaching of the target switching position by the gate is detected. The control apparatus according to the invention can be correspondingly designed to do this.

The tablet discharge can have at least one discharge channel as is known per se. In particular, the tablet discharge can have several discharge channels between which the gate can deflect the stream of tablets. Each discharge channel can lead to one of the tablet outlets. As already explained, the tablet outlets can for example lead to an outlet for bad tablets, for good tablets, or to a measuring apparatus for a sampling.

The gate can comprise at least one gate flap pivotably mounted in the at least one discharge channel of the tablet discharge between the first switching position and at least a second switching position. Such a gate flap is an elongated body which is preferably pivotably mounted in the region of its one end on the discharge channel. The opposite free end of the gate flap then executes the maximum pivoting movement. The free end of the gate flap can be arranged upstream from the pivot bearing viewed in the discharge direction of the tablets. The gate flap can for example consist of a metal material. This is known per se. Of course, the gate can also comprise several such gate flaps arranged sequentially in the direction of flow of the tablets in order for example to be able to switch between three discharge channels.

According to another embodiment, at least one discharge channel can have at least one section that expands in the discharge direction of the tablets, preferably that expands in steps. According to another embodiment, the at least one expanding section can be located upstream in the discharge direction of the tablets, preferably directly upstream, from the region swept by the gate flap, for example its free end, during its pivoting movement. It is moreover advantageous when at least one expanding section is provided that expands, preferably expands in steps, on opposing walls of the discharge channel. According to another embodiment, the expansion of the at least one expanding section can have a width of at least 10 mm, preferably at least 19 mm, and more preferably at least 25 mm. The width is measured in a direction perpendicular to the direction of flow of the tablets, or respectively the longitudinal axis of the discharge channel. In this case, the width is preferably at least as wide as the largest tablet to be conveyed through the discharge channel.

The aforementioned preferably stepwise expansion forms a switching bay. In particular, the width of the discharge channel increases here. The expansion can be located in the region of one or all target switching positions of the gate. The expansion is designed such that the clamping of tablets between the gate and an opposite wall of the discharge channel does not hinder the remaining stream of tablets. If the gate does not reach its target switching position because a tablet is clamped by the gate, the clamped tablet is already located within the expanded section of the discharge channel. This ensures that not reaching the target switching position because of a clamped tablet does not form a hindrance for the remaining stream of tablets. A tablet jam is very reliably prevented. The expanding section can in particular be designed such that when the target switching position is not reached by the gate when a tablet is clamped by the gate, the gate does not substantially project (inward) beyond the guide section of the discharge channel located directly upstream from the expanding section in the discharge direction of the tablets. This guide section can also be formed by a wall of the discharge channel or also by a gate, or respectively gate flap, located upstream in the discharge direction when there are several sequentially arranged gates or respectively gate flaps.

The invention also relates to a rotary tablet press comprising a rotor that can be rotated by means of a rotary drive, wherein the rotor has an upper punch guide for upper punches of the rotary tablet press, a lower punch guide for lower punches of the rotary tablet press and a die plate arranged between the punch guides, wherein the punches interact with cavities in the die plate, furthermore comprising a filling apparatus by means of which the filling material to be pressed is added to the cavities in the die plate, furthermore comprising at least one upper pressing apparatus and at least one lower pressing apparatus that, during operation, interact with the upper punches and the lower punches such that they press the filling material into tablets in the cavities in the die plate, moreover comprising an ejection apparatus in which the tablets generated in the cavities are ejected, and moreover comprising a tablet discharge that is fed the ejected tablets, wherein at least one gate according to the invention is arranged in the tablet discharge.

The method according to the invention can be performed with a gate according to the invention or a rotary tablet press according to the invention. Accordingly, the gate according to the invention or the rotary tablet press according to the invention can be designed to perform the method according to the invention.

BRIEF DESCRIPTION OF THE DRAWINGS

An exemplary embodiment of the invention is explained below in greater detail with reference to figures. Schematically.

The same reference numbers refer to the same objects in the figures unless indicated otherwise.

DETAILED DESCRIPTION OF THE INVENTION

Figure 1:
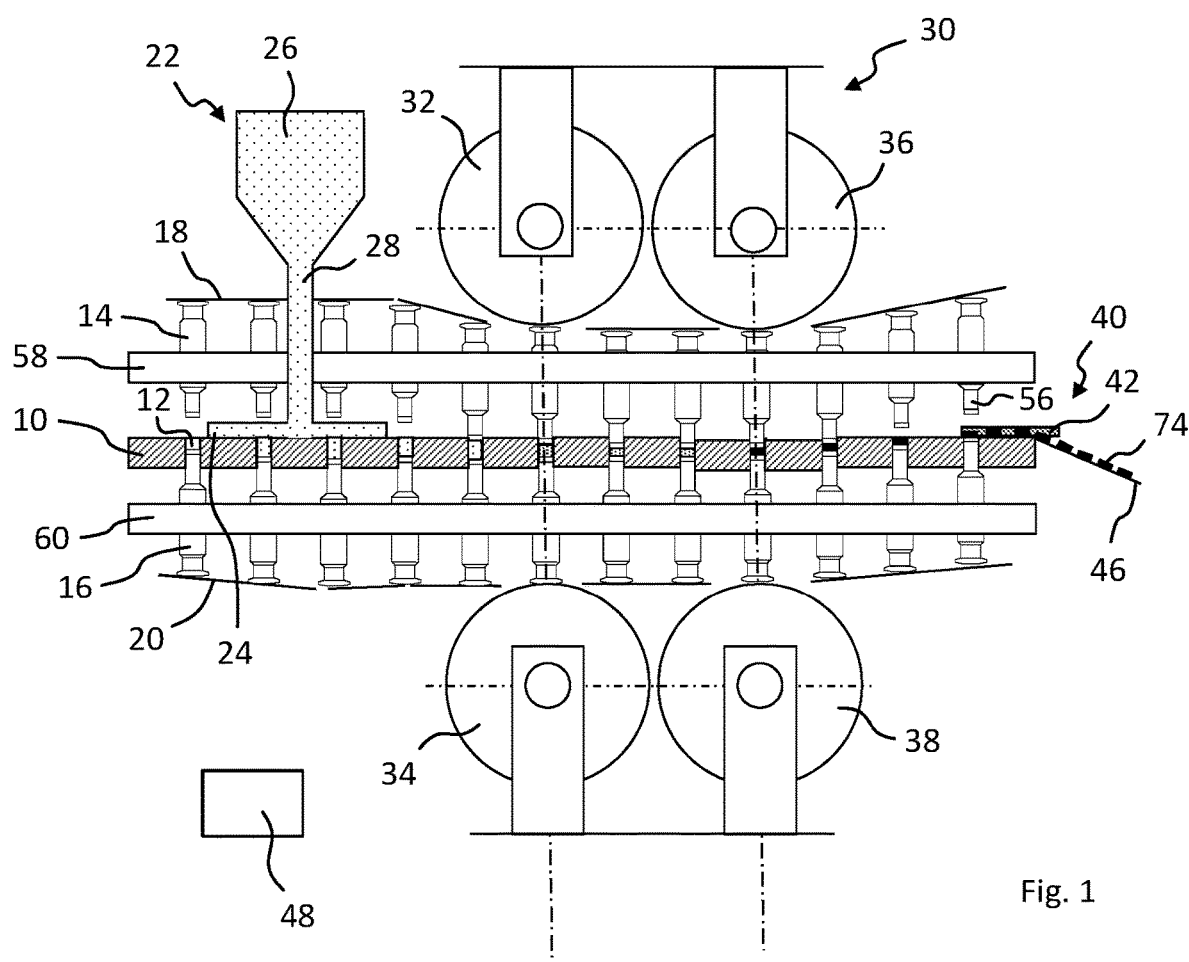
FIG. 1 illustrates a cross-sectional view of an embodiment of a rotary press.
Figure 2:
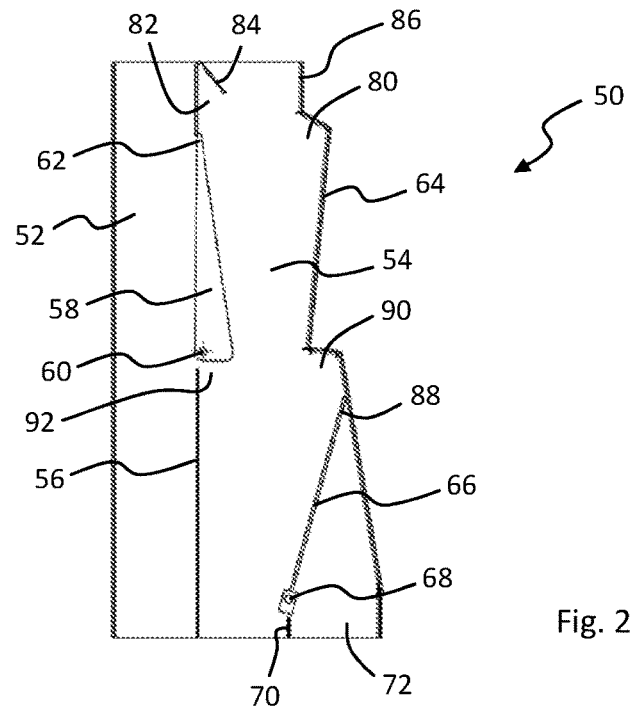
FIG. 2 illustrates a top plan view of an embodiment of a gate of the rotary tablet press shown in FIG. 1 in a first operating position.

The rotary tablet press shown in FIG. 1 comprises a rotor that is rotationally driven by a rotary drive (not shown) with a die plate 10 which has a plurality of cavities 12. The cavities 12 can for example be formed by holes in the die plate 10. Furthermore, the rotor comprises a plurality of upper punches 14 and lower punches 16 that rotate synchronously with the die plate 10. In each case, a pair consisting of an upper punch 14 and lower punch 16 is thus assigned to a cavity 12. The axial movement of the upper punches 14 and lower punches 16 during the rotation of the rotor is controlled by upper control cam elements 18 and lower control cam elements 20. The rotary tablet press moreover comprises a filling apparatus 22 which has a filling chamber 24. The filling apparatus 22 moreover comprises a funnel-shaped filling material reservoir 26 which is connected by a feed section 28 to the filling chamber 24. In this manner, the powdered filling material in the present example passes under the force of gravity from the filling material reservoir 26 via the feed section 28 into the filling chamber 24, and passes therefrom via a filling opening provided in the bottom side of the filling chamber 24 into the cavities 12 of the die plate 10, again under the force of gravity.

Moreover, the rotary tablet press comprises a pressing apparatus 30. The pressing apparatus 30 possesses a pre-pressing apparatus with an upper pre-pressing roller 32 and a lower pre-pressing roller 34, as well as a main pressing apparatus with an upper main pressing roller 36 and a lower main pressing roller 38. Furthermore, the rotary tablet press comprises an ejecting apparatus 40, in the present case with a scraper 42 which supplies the tablets 74 produced in the rotary tablet press to a tablet discharge 46.

A control apparatus for operating the rotary press is shown with reference number 48. The control apparatus 48 can for example comprise a computer processor, microprocessor, microcontroller, or similar device. The control apparatus 48 is connected by lines (not shown) to, inter alia, the rotary drive of the rotor.

A gate 50 shown in FIGS. 2 to 5 is located in the tablet discharge 46. The gate 50 has a first discharge channel 52 and a second discharge channel 54. The first and the second discharge channel 52, 54 are separated by a partition wall 56 from each other. A first gate flap 58 located in the partition wall 56 is mounted pivotably about a first pivot axis 60 between the first switching position shown in FIG. 2 and a second switching position (not shown) in which the free end 62 of the gate flap 58 lies against the opposite wall 64 of the second discharge channel 54. In FIGS. 2 to 5, tablets flow from top to bottom through the gate 50. Downstream from the first gate flap 58, a second gate flap 66 is pivotably mounted about a second pivot axis 68 in the second discharge channel 54 between a first switching position shown in FIG. 2 and a second switching position shown in FIG. 4. Downstream from the second gate flap 66, a partition wall 70 can be seen that defines a third discharge channel 72. Drives of a drive apparatus are provided such as electric motor or electromagnetic drives to pivot the first gate flap 58 and the second gate flap 66 between their respective first and second switching position. In addition, sensors (not shown) which are known per se are provided that detect the reaching of the respective end positions of the gate flaps 58, 66, i.e., the respective first switching position and the respective second switching position. The detection signals of the sensors are also applied to the control apparatus 48 in the shown example.

Figure 3:
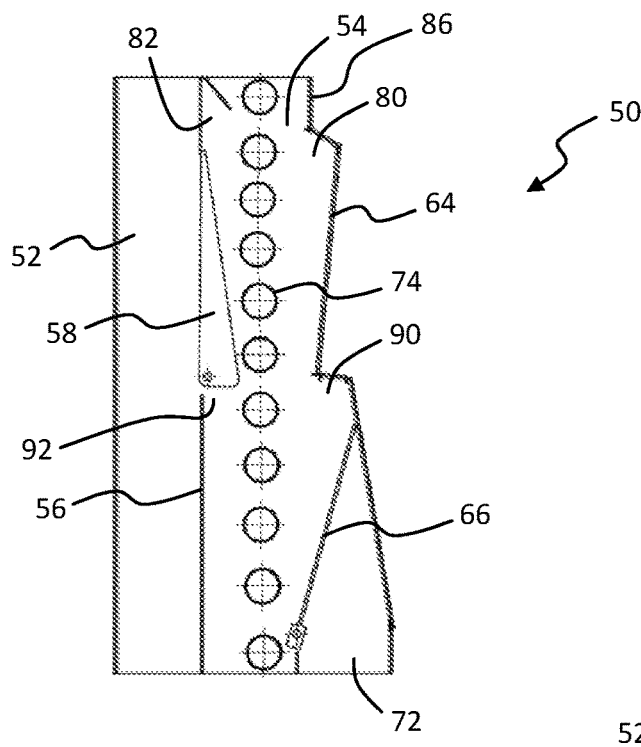
FIG. 3 illustrates the gate from FIG. 2 in a second operating position.
Figure 4:
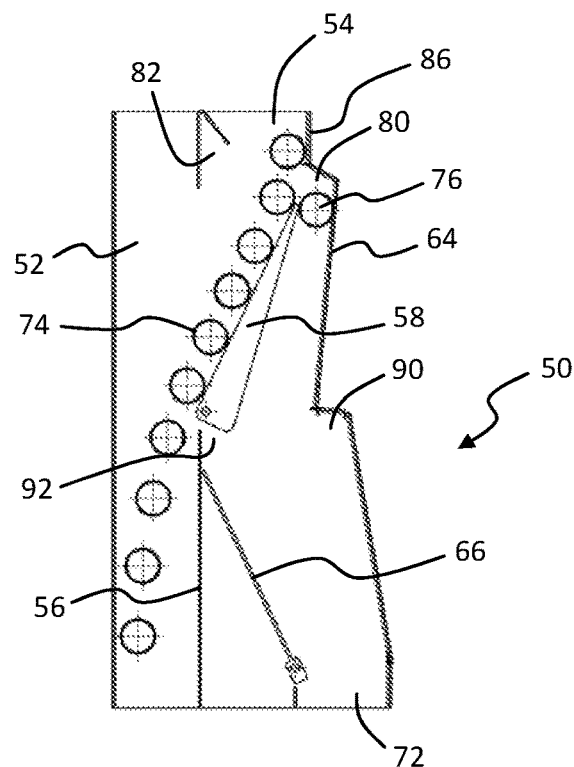
FIG. 4 illustrates the gate from FIG. 2 in a third operating position.
Figure 5:
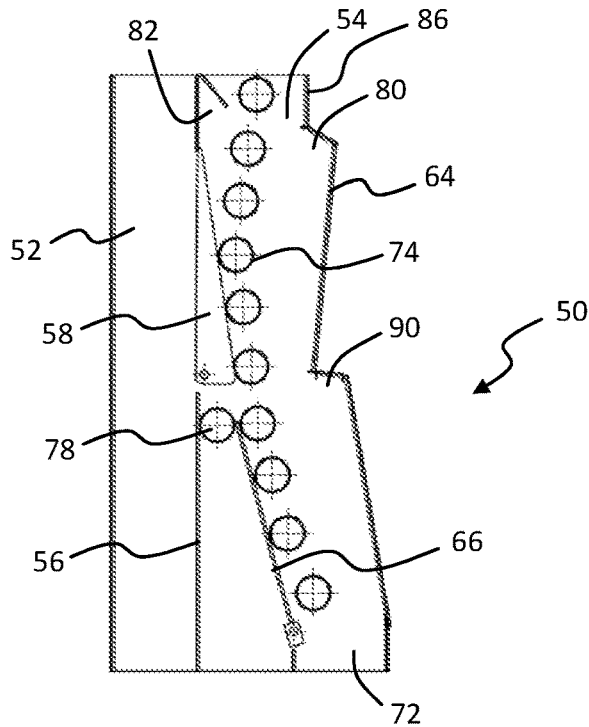
FIG. 5 illustrates the gate from FIG. 2 in a fourth operating position.

Tablets 74 which are discharged through the gate 50 for different operating states of the gate 50 are shown in FIGS. 3 to 5. As can be seen in FIG. 3, the tablets 74 run through the second discharge channel 54 when the first gate flap 58 and the second gate flap 66 are in the first switching position. If contrastingly the first gate flap 58 moves toward its second switching position as shown in FIG. 4, the stream of tablets 74 is deflected from the second discharge channel 54 into the first discharge channel 52. Only when the first gate flap 58 is located in its first switching position does the flow of tablets 74 reach the second gate flap 66. Depending on its switching position, this deflects the stream of tablets 74 into the third discharge channel 72 (see FIG. 5) or closes the access to the third discharge channel 72 so that the stream of tablets 74 can continue to flow through the second discharge channel 54.

The second discharge channel 54 can for example lead to a tablet outlet for good tablets. The third discharge channel 72 can for example lead to a tablet outlet for a sampling. The first discharge channel 52 can for example lead to a tablet outlet for bad tablets.

In FIG. 4, a tablet 76 clamped between the first gate flap 58 and the opposite wall 64 can be seen. The first gate flap 58 therefore cannot reach its second switching position. Not reaching the second switching position is detected by the respective sensor, and the control apparatus therefore emits a switching signal to the drive of the first gate flap 58 so that it partially pivots the gate flap 58 back toward the first switching position, i.e., counterclockwise in FIG. 4. The clamped tablet 76 is thereby released, and it can continue to flow. To accomplish this, a slight return movement of the gate flap 58 is sufficient for the tablet 76 to be released. Then the control apparatus controls the drive by again outputting a corresponding switching signal such that it moves the first gate flap 58 back into the second switching position that can now easily be reached due to the released tablet 76.

FIG. 5 shows the instance in which the second gate flap 66 clamps a tablet 78 between itself and the opposing partition wall 56 when moving out of its first switching position into its second switching position. Again, the second gate flap 66 cannot reach its second switching position. Due to a relevant detection signal of the associated sensor, or respectively its absence, the control apparatus 48 outputs a switching signal to the drive of the second gate flap 66 so that it moves the second gate flap 66 partially back toward its first switching position, i.e., pivots clockwise in FIG. 5. The clamped tablet 78 is thereby released, and it can flow. Again, a slight return movement of the gate flap 66 is sufficient for the tablet 78 to be released. Then the second gate flap 66 is moved by a corresponding switching signal from the control apparatus 48 back into its second switching position, wherein it can now fully reach it.

It can also be seen in FIGS. 2 to 5 that the second discharge channel 54 expands in width on both sides directly upstream from the region swept by the first gate flap 58 during its pivoting movement, in particular the region swept by its free end 62. The expanding sections are shown with reference numbers 80 and 82. In this context, it is discernible that the expanding section 82 is formed because an upstream constriction from a wall projection 84 terminates. The sections 80, 82 that expand stepwise in the shown example each substantially correspond in the shown example to the width of the tablets 74, 76, 78 to be diverted by the gate 50. As shown for example in FIG. 4 for the expanding section 80, these expanding sections 80, 82 cause the stream of tablets 74 to be unimpaired from the tablet 76 being clamped and the respective end position caused thereby from not being reached by the respective gate flap. Accordingly, the clamped tablet 76 is already located within the expanded section 80. The free end 62 of the first gate flap 58 basically does not project inwardly beyond the wall section 86 located directly upstream from the expanded section 80. In this respect, the expanded section 82 provided on the opposite side offers the same function.

There are also expanded sections 90, 92 in the second discharge channel 54 on opposing sides directly upstream from the region swept by the free end 88 of the second gate flap 66 during its pivoting movement. In this context, the expanded section 92 is formed by the end of the first gate flap 58—the bottom end in FIG. 2—of the constriction of the second discharge channel 54. In the same manner as explained above with reference to the first gate flap 58, the expanded sections 90, 92 also cause a tablet 78 clamped by the second gate flap 66 and the second gate flap 66 thereby being unable to reach the respective end position from impairing the stream of tablets 74. This is shown for example in FIG. 5 for the expansion 92. The expansion 90, 92 also substantially corresponds in its width to the diameter of the tablets 74, 76, 78 to be diverted by the gate 50.

LIST OF REFERENCE NUMBERS

10 Die plate
12 Cavities
14 Upper punches
16 Lower punches
18 Upper control cam elements
20 Lower control cam elements
22 Filling apparatus
24 Filling chamber
26 Filling material reservoir
28 Feed section
30 Pressing apparatus
32 Upper pre-pressing roller
34 Lower pre-pressing roller
36 Upper main pressing roller
38 Lower main pressing roller
40 Ejection apparatus
42 Scraper
46 Tablet discharge
48 Control apparatus
50 Gate
52 First discharge channel
54 Second discharge channel
56 Partition wall 58 First gate flap
60 First pivot axis
62 Free end
64 Wall
66 Second gate flap
68 Second pivot axis
70 Partition wall
72 Third discharge channel
74 Tablets
76 Tablet
78 Tablet
80 Expanded section
82 Expanded section
84 Wall projection
86 Wall section
88 Free end
90 Expanded section
92 Expanded section

The invention claimed is:

1. A tablet press with a tablet discharge, the tablet press comprising:
- a gate positioned in the tablet discharge and moveable between a first switching position and a second switching positon, the gate comprising,
    - a first discharge channel connected to a first tablet outlet, and
    - a second discharge channel connected to a second tablet outlet;
- a control apparatus configured to generate and output a plurality of switching signals;
- a drive apparatus configured receive the plurality of switching signals from the control apparatus and, in response, drive the gate between the first switching position in which tablets are fed to a first tablet outlet, and the second switching position in which tablets are fed to a second tablet outlet; and
- at least one sensor configured to,
    - generate a first detection signal at the first switching position and transmit the first detection signal to the control apparatus,
    - generate a second detection signal at the second switching position and transmit the second detection signal to the control apparatus, and
    - detect a tablet clamped by the gate against the tablet discharge, wherein, in response to the detected tablet clamped by the gate, the control apparatus outputs a switching signal to the drive apparatus to at least partially drive the gate back into a home position to unclamp the tablet and inhibit a tablet jam and an interruption in tablet production, wherein the control apparatus subsequently outputs another switching signal to the drive apparatus to signal the drive apparatus to drive the gate into a target position, and wherein the home position is defined as the one of the first switching position and the second switching position that the gate is initially in, and wherein the target position is defined as the one of the first switching position and the second switching position that the gate is being moved to.

2. The tablet press according to claim 1, further comprising at least a third discharge channel.

3. The tablet press according to claim 2, wherein the gate comprises at least one gate flap pivotably mounted within the at least one of the first and second discharge channel of the tablet discharge and configured to sweep a region to direct tablets into the at least one of the first and second discharge channel.

4. The tablet press according to claim 3, wherein at least one of the first, second and at least the third discharge channel comprises at least one section that expands along a tablet discharge direction.

5. The tablet press according to claim 4, wherein the at least one section that expands is configured to expand in a stepwise fashion.

6. The tablet press according to claim 4, wherein the at least one section that expands is located upstream from the region swept by the gate flap during its pivoting movement.

7. The tablet press according to claim 4, wherein the at least one section that expands is positioned on opposing walls of the at least one of the first, second and at least the third discharge channel.

8. The tablet press according to claim 4, wherein the at least one section that expands is configured to expand to a width of at least 10 mm.

9. The tablet press according to claim 1, wherein the tablet clamped by the gate is detected by an absence of the second detection signal.

* * * * *